United States Patent
Schubert et al.

(10) Patent No.: US 9,611,942 B2
(45) Date of Patent: Apr. 4, 2017

(54) VALVE HAVING A DEFORMABLE PART AND USE OF THE VALVE

(75) Inventors: Michael Schubert, Wels (AT); Reinhard Busch, Steyr (AT); Michael Nader, Rheinbach (DE)

(73) Assignee: Christoph Artner, Lieboch (AT)

( * ) Notice: Subject to any disclaimer, the term of this patent is extended or adjusted under 35 U.S.C. 154(b) by 519 days.

(21) Appl. No.: 14/002,401

(22) PCT Filed: Mar. 1, 2012

(86) PCT No.: PCT/AT2012/050027
§ 371 (c)(1),
(2), (4) Date: Oct. 3, 2013

(87) PCT Pub. No.: WO2012/116390
PCT Pub. Date: Sep. 7, 2012

(65) Prior Publication Data
US 2014/0053930 A1    Feb. 27, 2014

(30) Foreign Application Priority Data

Mar. 2, 2011  (AT) .................................. A 278/2011

(51) Int. Cl.
*G01N 30/20*      (2006.01)
*F16K 11/00*     (2006.01)
(Continued)

(52) U.S. Cl.
CPC .......... *F16K 11/00* (2013.01); *F16K 11/0743* (2013.01); *G01N 30/20* (2013.01);
(Continued)

(58) Field of Classification Search
None
See application file for complete search history.

(56) References Cited

U.S. PATENT DOCUMENTS 3,707,991 A    1/1973  Shapiro
4,464,340 A *  8/1984  Lennox et al. .............. 422/68.1
(Continued)

FOREIGN PATENT DOCUMENTS

DE   10 2008 042 252 A1   4/2009
EP        0 409 522 A2    1/1991
(Continued)

OTHER PUBLICATIONS

International Search Report of PCT/AT2012/050027, date of mailing Jul. 16, 2012.
(Continued)

*Primary Examiner* — Robert R Raevis
(74) *Attorney, Agent, or Firm* — Collard & Roe, P.C.

(57) ABSTRACT

The invention relates to a valve, in particular a sample injection valve, for a device (1) for synthesizing, analyzing, and/or separating, comprising at least three liquid connections (3', 4', 5', 6', 7', 7"), a housing (8) as a valve part, and a valve body (9) as another valve part for selectively connecting the liquid connections (3', 4', 5', 6', 7', 7") by means of at least one flow channel (10, 11, 12) bounded at least partially by sealing surfaces (10', 11', 12') between the housing (8) and the valve body (9), wherein the housing (8) and/or the valve body (9) are supported in such a way as to be movable relative to each other. In order to create a one-way valve, at least one valve part (8 or 9) adjacent to the sealing surface (10', 11', 12') and made of a plastic material can be plastically deformed according to a relative position (9'), in particular of the valve body (9), in order to be able to withstand the elevated pressure loads in the flow channel (10, 11, 12) in a liquid-tight manner in the relative position (9'), in particular of the valve body (9).

9 Claims, 4 Drawing Sheets

(51) Int. Cl.
*F16K 11/074*  (2006.01)
*G01N 35/10*  (2006.01)
*G01N 30/26*  (2006.01)

(52) U.S. Cl.
CPC ......... *G01N 30/26* (2013.01); *G01N 35/1097* (2013.01); *G01N 2030/201* (2013.01); *G01N 2030/202* (2013.01); *Y10T 137/86493* (2015.04)

(56) References Cited

U.S. PATENT DOCUMENTS

| | | |
|---|---|---|
| 5,010,921 A | 4/1991 | Nohl |
| 5,419,208 A | 5/1995 | Schick |
| 8,196,896 B2 | 6/2012 | Keene |
| 2002/0195150 A1 | 12/2002 | Schick |
| 2011/0272855 A1 | 11/2011 | Luongo et al. |

FOREIGN PATENT DOCUMENTS

| | | |
|---|---|---|
| SU | 773359 A1 | 10/1980 |
| WO | WO 2005/089124 A2 | 9/2005 |
| WO | WO 2010/051297 A1 | 5/2010 |

OTHER PUBLICATIONS

International Preliminary Report on Patentability of PCT/AT2012/050027, date of issuance Sep. 3, 2013.
Austrian Office Action of A 278/2011, dated Sep. 20, 2011, with English translation of relevant parts.
Response to European Patent Office in EP 1271855.7, dated Oct. 2, 2013, with English translation of relevant parts.

* cited by examiner

VALVE HAVING A DEFORMABLE PART AND USE OF THE VALVE

CROSS REFERENCE TO RELATED APPLICATIONS

This application is the National Stage of PCT/AT2012/050027 filed on Mar. 1, 2012, which claims priority under 35 U.S.C. §119 of Austrian Application No. A 278/2011 filed on Mar. 2, 2011, the disclosure of which is incorporated by reference. The international application under PCT article 21(2) was not published in English.

TECHNICAL FIELD

The invention relates to a valve, particularly a sample application valve, for an apparatus for synthesis, analysis and/or separation purposes, having at least three liquid connectors, having a housing as a valve part, and having a valve body as another valve part, for optional connection of the liquid connectors by way of at least one flow channel delimited at least in part by sealing surfaces between housing and valve body, wherein housing and/or valve body are mounted so as to be movable relative to one another.

STATE OF THE ART

In the case of sample separation devices, for example in the case of an HPLC (high-performance liquid chromatography) device, it is known to use a valve, particularly a sample application valve, for selection of different columns of a fluid sample phase (DE102008042252A1). In this connection, pumps can produce a pressure of up to 1000 bar for movement of the mobile phase, so that the sample application valve must meet significant material and seal demands. Therefore complex and comparatively expensive valve embodiments are known from the state of the art, and therefore use as a disposable valve is prohibited for these valves. However, it is a disadvantage that multiple use of the valves requires significant cleaning effort. The latter, in particular, is of decisive importance for the result of the sample separation device, so that the sample application valve has particular importance for an apparatus for synthesis, analysis and/or separation purposes. Further valves are known from U.S. Pat. No. 3,707,991 A and from SU773359A1.

Presentation of the Invention

It is therefore the task of the invention to change the design of a valve for an apparatus for synthesis, analysis and/or separation purposes, of the type described initially, in such a manner that a disposable valve can be made possible with a simple design and therefore advantageous costs. Furthermore, cleaning of the valve is no longer supposed to be necessary.

The invention accomplishes the stated task in that at least one valve part that borders on the sealing surface and has a plastic material is configured to be plastically deformable, as a function of a relative position, particularly of the valve body, in order to be able to withstand increased pressure stresses in the flow channel, in liquid-tight manner, in this relative position, particularly of the valve body.

If at least one valve part that borders on the sealing surface and has a plastic material is configured to be plastically deformable, as a function of a relative position, particularly of the valve body, then it is possible to create a particularly pressure-stable valve in simple design manner. This irreversible deformation of the plastic can specifically be utilized to withstand increased pressure stresses in the flow channel, in liquid-tight manner, in this relative position (as compared with other relative positions, particularly of the valve body relative to the housing), so that even production-related tolerances can be balanced out. Such a valve can therefore guarantee transfer of high pressures at least in one relative position, particularly of its valve body, so that a consistent flow channel can be made available, for example in order to thereby transfer a mobile phase into the column. In this connection, it is unimportant for the invention whether the valve part, the housing, or even a seal provided between the valve part and/or the housing passes through the plastic deformation of the plastic material, in order to thereby create the pressure-stressed and tight flow channel or to guarantee a stable valve. The fact of the possible loss of function of the valve as the result of its irreversible deformation plays a subordinate role for the invention—after all, the valve has fulfilled its function for synthesis, analysis and/or separation purposes after its high-pressure transfer of the mobile phase. However, as a result of this option of permitting plastic deformation, the valve according to the invention can be kept very simple in terms of design and therefore cost-advantageous as compared with known valves, so that the possibility of a disposable valve can also open up. Complicated cleaning of the valve can be eliminated in this way, and this significantly simplifies the methods for synthesis, analysis and/or separation purposes. Furthermore, using the disposable valve, the risk of falsification of the results due to contaminants can be kept low, which can improve the stability of the methods and apparatuses. The valve according to the invention is therefore characterized not only by its design simplicity and cost advantages, but also can significantly simplify the operation of an apparatus for synthesis, analysis and/or separation purposes, with its use as a disposable valve.

Particularly simple operation conditions can result if the valve body is mounted in the housing by way of a screw connection, so as to rotate. In particular, the degree of plastic deformation can be adjusted, in simple manner, by means of the pitch of the screw connection, which guarantees a reproducibly uniform relative position of the valve body in its high-pressure position. Furthermore, such a rotation valve also opens up design simplicity, because the face side of the valve body or also its mantle sides can be used for this purpose.

If the valve body is configured to be plastically deformable, at least in part, the design effort can be reduced even further, in that the guide of the body is used to ensure plastic deformation precisely on every sealing surface that is supposed to delimit the flow channel with increased pressure resistance. Furthermore, the valve body can be produced in relatively simple manner, and is generally not subject to any special dependencies during assembly of the valve, relative to other valve parts. The accompanying reduced production effort can furthermore ensure a reduction in the production costs, so that the valve according to the invention can additionally be suitable as a disposable valve.

If the valve body mounted in the housing so as to rotate has at least one face-side recess for at least one flow channel, then a stable flow channel can be ensured in the region of the sealing surface, despite plastic deformations. Dimensional changes at the boundary surfaces of the valve parts can specifically be absorbed by the flow channel, in simple manner, in this way, without having to expect wear of this channel, which would be disadvantageous.

A particularly tight connection between housing and valve body can be created if the valve body forms at least one plastically deformable sealing lip, which follows at least one sealing surface. Furthermore, by means of this one-piece design of the valve body with its sealing lip (no seal that has to be inserted is required any longer), the design effort and therefore the costs of the disposable valve can be reduced. Furthermore, in this manner, sufficient plastic deformability in the region of the sealing surface can be ensured, without having to expect an interruption of the flow channel. The stability of the valve can thereby be clearly increased.

Simple design conditions and great chemical resistance result, if the housing and/or the valve body consist(s) of polyetheretherketone (PEEK). Furthermore, in this way, plastic deformation can be possible on both adjacent valve parts, thereby making it possible to create a particularly liquid-tight connection. High liquid pressures can therefore be absorbed by the valve, without further design measures, and therefore these valves can be particularly suitable for an apparatus for synthesis, analysis and/or separation purposes.

In order to avoid fittings for a connection of hose lines to the valve, the valve can have a sleeve that is divided into two parts and encloses the housing at least in the region of the liquid connectors, which sleeve forms accommodations for connection of elastic hose lines, directed particularly in alignment toward the insertion guides of the liquid connectors. The hose lines can thereby be accommodated and held by the ring, whereby liquid-tight installation of the hose lines on the valve is made possible using the elastic widening of the hose lines under pressure stress. In this way, a particularly cost-advantageous valve can be created.

If the accommodations have surface structures for holding the accommodated hose lines in place, then holding of the hose lines can be ensured even at high pressure stresses, with a simple design and in cost-advantageous manner. Furthermore, the stability of the valve with regard to high pressure stresses can be further improved in this way. Simplified design conditions occur if a holding thread forms such surface structures, which thread can press itself into the elastic hose lines, for example.

The invention has particularly proven itself if this valve is used as a disposable valve in an apparatus for high-performance liquid chromatography (HPLC). Complicated cleaning of the valve can thereby be eliminated, and therefore such methods can become particularly easy to handle and reliable in terms of their results.

BRIEF DESCRIPTION OF THE DRAWING

The object of the invention is shown in the figures, as an example, using an exemplary embodiment. The figures show.

WAY TO IMPLEMENT THE INVENTION

Figure 1:
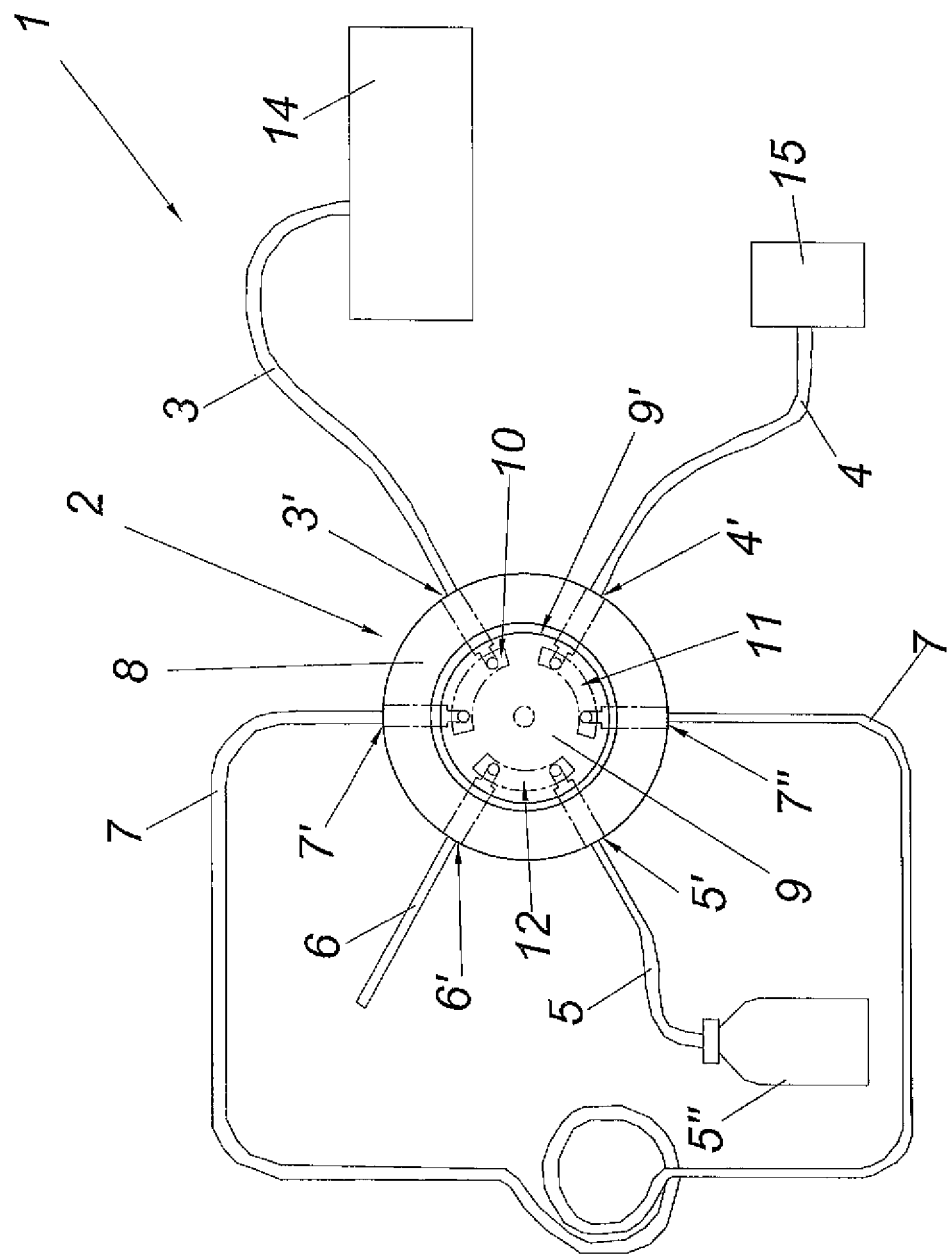
FIG. 1 an apparatus for synthesis, analysis and/or separation purposes, having the valve according to the invention in its "inject" position, FIG. 2 a cross-section of the valve plane with the inlets 7' and 7" of the apparatus shown in FIG. 1, but in the "load" position, FIG. 3 a cross-section of the valve according to FIG. 1, in its "inject" position, with plastic deformation of a valve part, FIG. 4 a face view of the valve body, FIG. 5 an enlarged view of a detail section through the valve body according to FIG. 4, and FIG. 6 a top view of the valve without the valve body, partly opened up.
Figure 2:
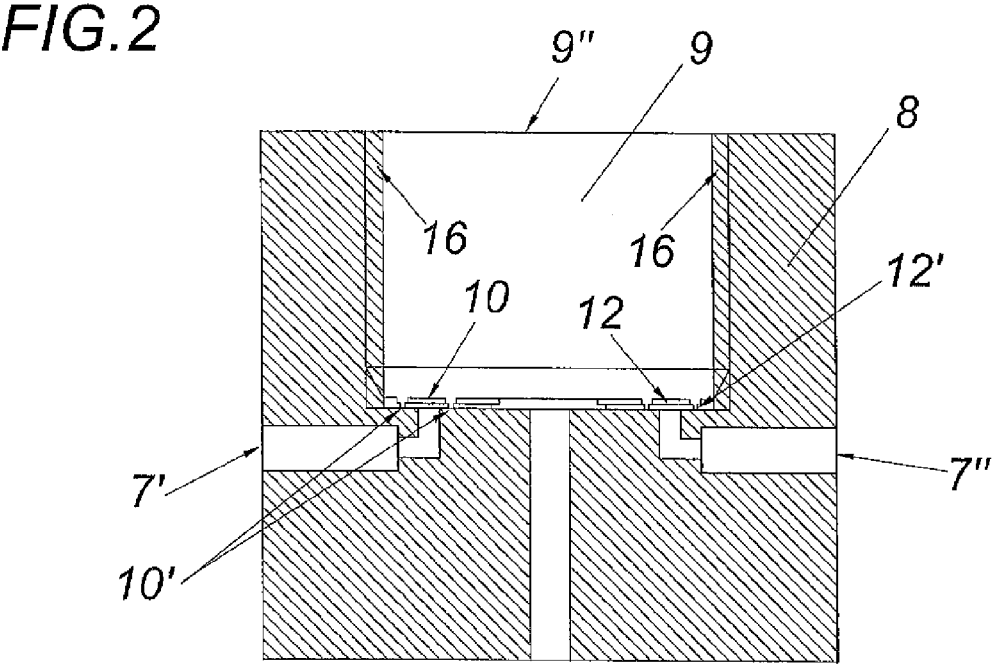
Figure 3:
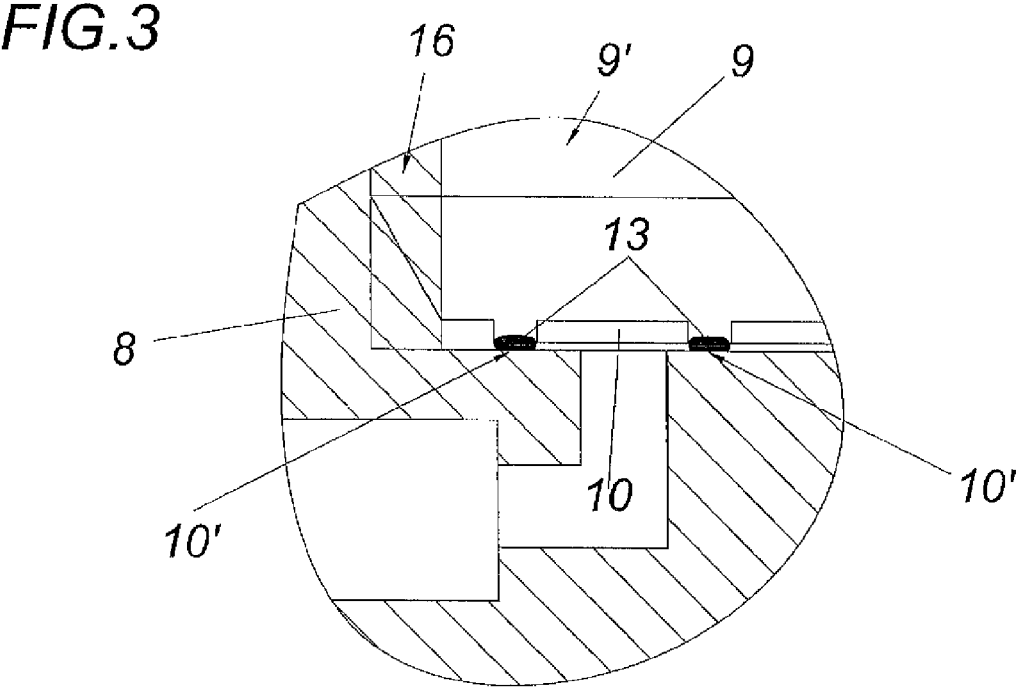

The valve 2 shown in FIG. 1, as an example, in connection with an apparatus 1 for high-performance liquid chromatography HPLC, is connected with multiple hose lines 3, 4, 5, 6, and 7. For this purpose, the valve 2 has multiple liquid connectors 3', 4', 5', 6', 7', and 7", which are provided on the housing 8. A valve body 9 mounted to be movable, relative to the housing 8, is provided in the housing 8, as can be seen in FIG. 2. A hose line 5, which is connected with a waste container 5", is also provided as an example. On the basis of its relative position 9', 9", the liquid connectors 3', 4', 5', 6', 7', and 7" can optionally be connected, whereby a relative position 9' can be seen in FIG. 1, and a different relative position 9" can be seen in FIG. 2. The relative position 9" is required to be able to apply the sample to the loop line 7 by way of the hose line 6 ("load"). Flow channels 10, 11, 12 result for this purpose between the liquid connectors 3', 4', 5', 6', 7', and 7", in each instance, whereby these flow channels 10, 11, 12 are also delimited by sealing surfaces 10', 11', 12' between housing 8 and valve body 9. These sealing surfaces 10', 11', 12' can particularly be seen in FIGS. 3, 4, and 5, whereby these have also been identified as the connection surface of the valve parts 8, 9 that interact, in this regard, for the sake of clarity. At low pressure demands on the valve 2, a low surface pressure between the valve parts, i.e. between the housing 8 and the valve body 9, at the sealing surfaces 10', 11', 12', has proven to be sufficient. In order to create such a low surface pressure, elastic deformation of the valve parts 8 and/or 9 is also possible. For example, such a low surface pressure is sufficient if the valve is being brought into the "load" position (relative position 9"), because here, only slight pressures need to be withstood. If, however, the flow channels 10, 11, 12 must withstand increased pressure demands, as is required for mastering an HPLC purification pressure of 200 bar, for example, it is known that significant design effort is required. Currently known valves are therefore not suitable as disposable valves, particularly if one is thinking in the direction of a plastic material for the valve parts 8 and 9, in order to thereby create a cost-advantageous valve 2. According to the invention, these disadvantages are overcome in that at least one valve part 8 and/or 9 that borders on the sealing surface 10', 11', 12' and has a plastic material is configured to be plastically deformable, as a function of a relative position 9' of the valve body. According to FIG. 3, it is evident that the valve body 9, as a valve part, is subject to plastic deformation 13. As a result of this plastic deformation 13, increased pressure stresses in the flow channel 10, 11 and/or 12 can be withstood, in liquid-tight manner in this relative position 9', as compared with other relative positions 9" of the valve body 9. Particularly in the case of the flow channels 10 and 11, this is important, because here the pump 14 must press the liquid (sample) into a column 15 at elevated pressure, by way of the loop line 7 (sample loop) ("inject" position of the valve 2). Since this represents the end position of the valve 2, its plastic deformation 13 and therefore its loss of function are also unimportant. What is significant, however, is that a disposable valve 2 can be created by means of the simple design, which valve requires no cleaning and is therefore particularly advantageous as compared with the state of the art.

The valve body 9 is mounted in the housing 8 by way of a screw connection 16, so as to rotate, in order to thereby allow different relative positions 9', 9" of the valve body 9 in comparison with the housing 8, with a simple design. In particular, however, a reproducibly increasing surface pressure on the sealing surfaces 10', 11', 12' can be made possible by way of the screw connection 16. This leads, among other things, to being able to ensure a reproducible plastic deformation for a sealed flow channel. The valve 2 can thereby distinguish itself by advantageous costs and precision, as well as stability.

Figure 4:
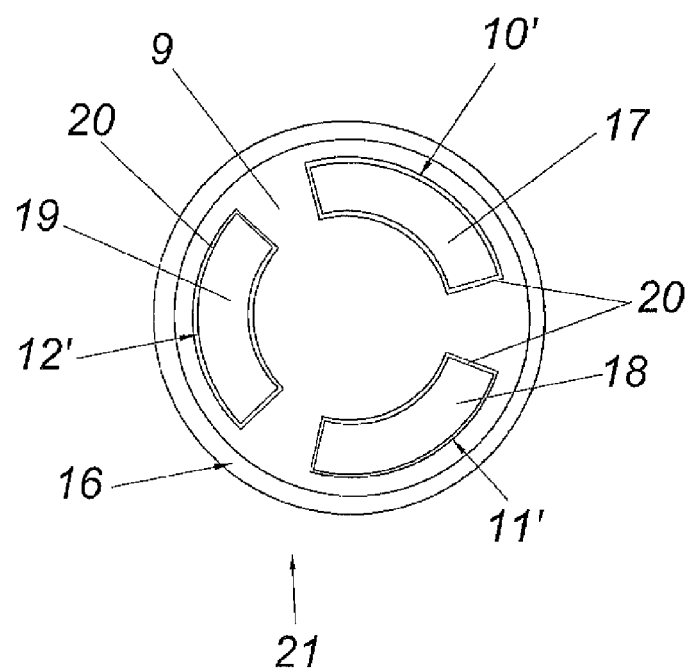

For the sake of simple production, the valve body 9 has face-side recesses 17, 18, 19 for the flow channels 10, 11, and 12, as can be seen in FIG. 4. In this way, stable flow channels 10, 11 or 12 can be ensured despite plastic deformations in the region of the sealing surfaces 10', 11', and 12'.

Figure 5:
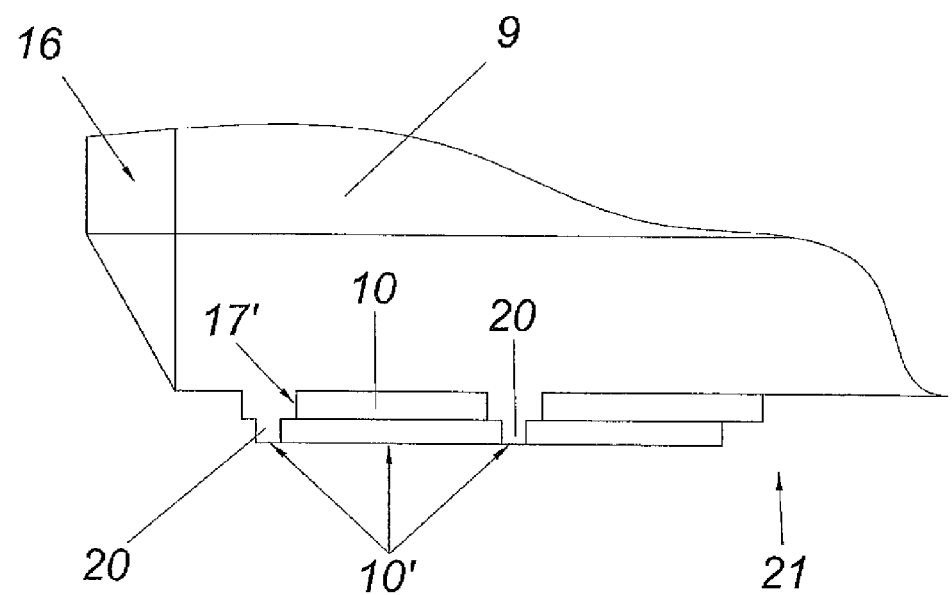

The danger of interruption of a flow channel 10, 11 or 12 can be clearly reduced by means of plastic deformation in the region of its sealing surface 10', 11' or 12', if the valve body forms a plastically deformable sealing lip 20 that follows the sealing surface 10', as can particularly be seen in FIG. 5. In FIG. 4, it is evident that this sealing lip 20 is also provided in the case of the other flow channels 11 and 12. Furthermore, the possibilities for plastic deformability of the valve body 9 can be adjusted by way of the configuration of the sealing lip 20, in simple manner. In addition, the valve bodies 9 and the sealing lip 20 are configured in one piece, so that there is design simplicity, particularly if the entire valve body 9 (with its sealing lip) consists of a plastic material and therefore can be produced, for example, using an injection-molding method, in one method step.

Polyetheretherketone (PEEK) has distinguished itself as a plastic material for the housing 8 and the valve body 9, in order to thereby create a suitable and cost-advantageous sample application valve 2 for an apparatus 1 for high-performance liquid chromatography (HPLC).

Figure 6:
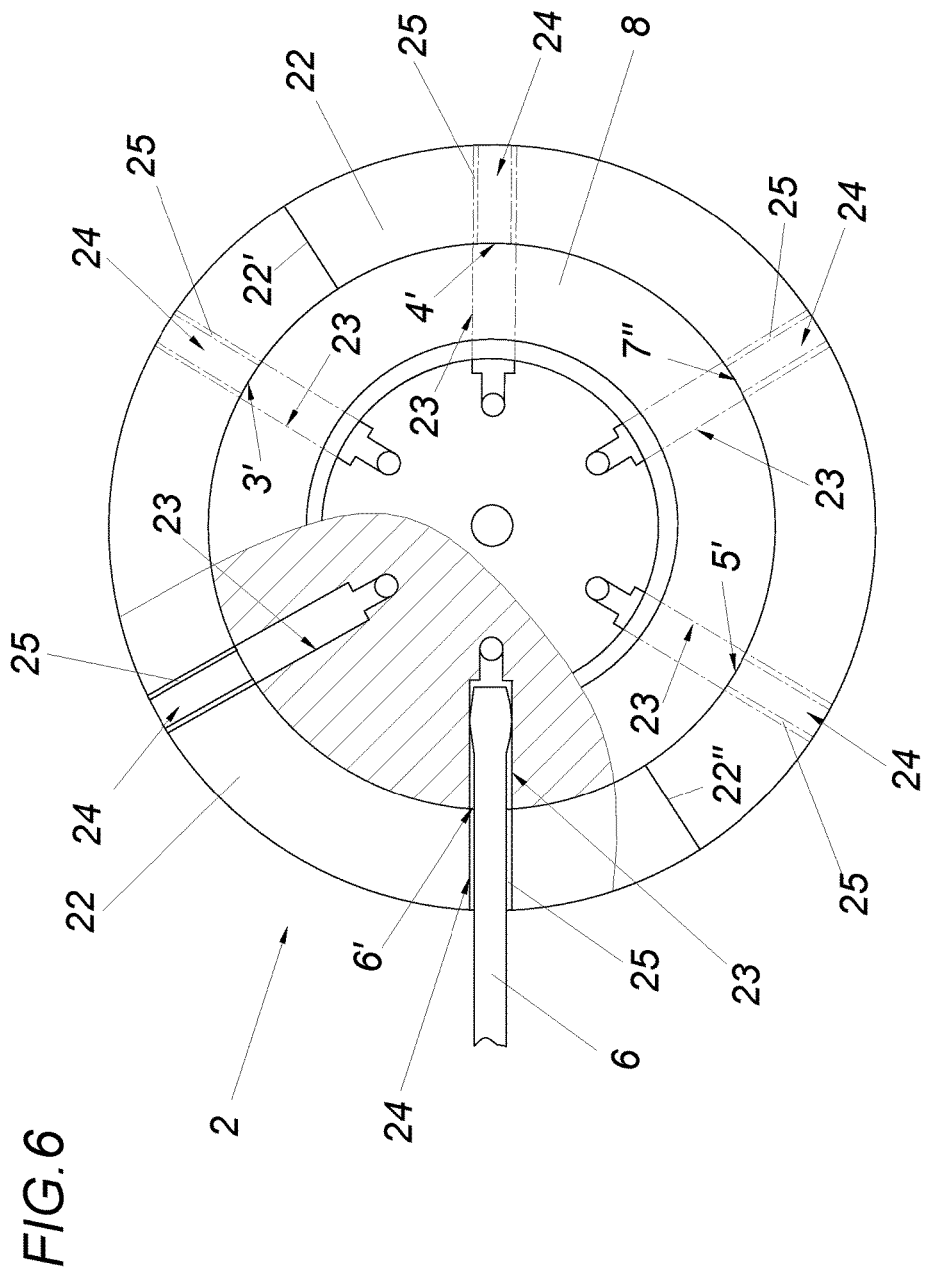

To connect the elastic hose lines 3, 4, 5, 6, and 7, a sleeve 22 is provided around the housing 8, whereby according to FIG. 6, for the sake of simplicity, only one hose line 6 is shown. The sleeve 22 is structured to be divided into two parts—indicated with the parting surface 22' and/or the parting surface 22"—so that the sleeve can be easily removed from the housing 8. Particularly with regard to the parting surface 22", it can therefore be seen that the opened-up region runs along this parting surface 22", and therefore no section lines can be seen in this opened-up region. The parting surface 22", in particular, allows simple connection of the hose lines 3, 4, 5, 6, and to the valve 2. The sleeve 22 forms accommodations 24 for connection of the elastic hose lines 3, 4, 5, 6, 7, directly in alignment toward the insertion openings 23 of the liquid connectors 3', 4', 5', 6', 7', 7". The parting 22" of the sleeve 22 in the plane of the accommodation 24, in particular, is advantageous for the simple connection possibility of the hose lines 3, 4, 5, 6, 7.

Because the elastic hose lines 3, 4, 5, and 7 widen under pressure stress, as can be seen for the hose line 6, a liquid-tight connection of the hoses to the valve 2 can be made possible. The sleeve 22 now holds the hose line 3, 4, 5, 6, and 7 in place on the valve 2, in that its accommodations 24 are each provided with a holding thread 25 as a surface structure for hooking engagement with the accommodated elastic hose line 3, 4, 5, 6 or 7, in each instance. This is particularly advantageous if the hose lines 3, 4, 5, 6, 7 consist of a plastic material.

The invention claimed is:

1. A sample application valve for an apparatus for synthesis, analysis and/or separation purposes, the valve having at least three liquid connectors, having a housing as a valve part, and having a valve body as another valve part, for optional connection of the liquid connectors by way of at least one flow channel delimited at least in part by sealing surfaces between housing and valve body, wherein housing and/or valve body are mounted so as to be movable relative to one another, wherein at least one valve part that borders on the sealing surfaces and has a plastic material is configured to be plastically deformable, as a function of a relative position of the valve body, in order to be able to withstand increased pressure stresses in the flow channel, in liquid-tight manner, in this relative position of the valve body, wherein in this relative position the at least one valve part plastically deforms irreversibly to withstand the increased pressure stress in the flow channel.

2. Valve according to claim 1, wherein the valve body is mounted in the housing by way of a screw connection, so as to rotate.

3. Valve according to claim 1, wherein the valve body is configured to be plastically deformable at least in part.

4. Valve according to claim 1, wherein the valve body mounted in the housing so as to rotate has at least one face-side recess for at least one flow channel.

5. Valve according to claim 1, wherein the valve body forms at least one plastically deformable sealing lip, which follows at least one sealing surface.

6. Valve according to claim 1, wherein at least one of the housing and the valve body comprises polyetheretherketone (PEEK).

7. Valve according to claim 1, wherein each liquid connectors includes an insertion opening and the valve has a sleeve that is divided into two parts and encloses the housing at least in the region of the liquid connectors, which sleeve forms accommodations for connection of elastic hose lines, directed in alignment toward the insertion openings of the liquid connectors.

8. Valve according to claim 7, wherein the accommodations have holding threads for holding the accommodated hose lines in place.

9. An apparatus for high-performance liquid chromatography, the apparatus comprising a valve according to claim 1.

* * * * *